United States Patent
Wu et al.

(10) Patent No.: US 6,235,874 B1
(45) Date of Patent: May 22, 2001

(54) PRODUCTION OF BIOLOGICALLY ACTIVE RECOMBINANT INSULIN-LIKE GROWTH FACTOR II POLYPEPTIDES

(75) Inventors: Jen-Leih Wu; Jyh-Yih Chen, both of Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/383,212

(22) Filed: Aug. 26, 1999

Related U.S. Application Data (63) Continuation-in-part of application No. 09/003,708, filed on Jan. 7, 1998.
(60) Provisional application No. 60/034,736, filed on Jan. 10, 1997.

(51) Int. Cl.$^7$ .......................... C07K 14/65; C12N 15/17; C12N 15/63
(52) U.S. Cl. .................... 530/303; 435/69.4; 435/320.1; 930/10
(58) Field of Search .................. 530/303; 435/320.1, 435/69.4; 930/10

(56) References Cited

U.S. PATENT DOCUMENTS 5,476,779 * 12/1995 Chen et al. .

OTHER PUBLICATIONS

DNA and Cell Biology J.Y. Chen et al. Production of Biologically Active Recombinant Tilapia Insulin–Like Growth Factor–II Polypeptides in *Escherichia coli* Cell and Characterization of the Genomic Structure of the Coding Region 16:–883–892.

DNA Alane Gray et al. Tissue–Specific and Developmentally Regulated Transcription of the Insulin–Like Growth Factor 2 Gene vol. 6, No.4 1987.

Histo–chemistry Reinecke et al. IGF–2–like peptides are present in insulin cells of the elasmobranchian endocrine pancreas: an immunohistochemical and chromatographic study 102:365–371 (1994).

Proc. Natl. Acad. Sci. USA Michael Shamblott Identification of a second insulin–like growth factor in a fish species 89:8913–8917.

DNA and Cell Vadim Kavsan Structure of the Chum Salmon Insulin–Like Growth Factor I Gene 12:729–737 Biology.

* cited by examiner

*Primary Examiner*—Christine J. Saoud
(74) *Attorney, Agent, or Firm*—Fei-Fei Chao; Venable, Baetjer, Howard & Civiletti, LLP (57) ABSTRACT

The present invention relates to the finding and construction of fish insulin-like growth factor II (IGF-II) cDNAs which can be cloned and expressed in cells. This invention also relates to the production of biologically active fish IGF-II polypeptides by a gene expression system using fish IGF-II cDNAs. The fish IGF-II cDNAs have 1977 bp which transcribe into a prepeptide (signal peptide), and B, C, A, D, E domain peptides. The fish mature IGF-II is a single polypeptide containing the $NH_2$—B—C—A—D—COOH domains. The mature IGF-II polypeptide is 7 kDa in weight and has 70 amino acids. The fish recombinant IGF-II cDNA can be cloned and expressed in *E. coli*, yeast, baculovirus, and fish cells. The isolated and purified IGF-II E domain peptide has mitogenic and anti-tumor activity.

3 Claims, 8 Drawing Sheets

```
1    gaattcgcggccgcctaactcacctgcaatcacaccaaataattcccacatttg
                    *
61   actactgccatctgacatggaaaccagcaaagatacggacatcactcactttgccacac
                    M  E  T  Q  Q  R  Y  G  H  H  S  L  C  H  T
121  ctgccggagaacgcagaacagcagaatgaaggtccagaggatgtcttcgacgagtcgggc
     C  R  R  T  Q  N  S  R  M  K  V  Q  R  M  S  S  T  S  R  A
181  gctgctctttgcactggccctgacgtctctacgtagtggaaatggcctcggcgagacgct
     L  L  F  A  L  A  L  T  L  Y  V  V  E  M  A  S  A  E  T  L
241  gtgtggggagaactggtgatgcgctgcagtttgtctgtgaagacagagggctttatt
     C  G  G  E  L  V  D  A  L  Q  F  V  C  E  D  R  G  F  Y  F
301  cagtaggccaaccagcaggggtaacaaccgacgCCcccagacccgtgggatcgtagagga
     S  R  P  T  S  R  G  N  N  R  R  P  Q  T  R  G  I  V  E  E
361  gtgttgtttccgtagctgtgacctcaacctactgagcagtactgtgccaacctgccaa
     C  C  F  R  S  C  D  L  N  L  E  Q  Y  C  A  K  P  A  K
421  gtccgaaaggacgtgtcagcacctctacaggtcataccggtgatgcccgcactaaa
     S  E  R  D  V  S  A  T  S  L  Q  V  I  P  V  M  P  A  L  K
```

FIG.1A

```
481  acaggaagttccgaagaagcaacatgtgaccgtgaagtattccaaatacgaggtgtggca
      Q  E  V  P  K  K  Q  H  V  T  V  K  Y  S  K  Y  E  V  W  Q 541  gaggaaggcggcccagcggctccggagggtgtccccgccattctgagggccagaaagta
      R  K  A  A  Q  R  L  R  R  G  V  P  A  I  L  R  A  R  K  Y 601  taagaggcacgcggagaagattaaagccaaggagcaggctatcttccacaggcccctgat
      K  R  H  A  E  K  I  K  A  K  E  Q  A  I  F  H  R  P  L  I 661  cagccttcctagcaagctgcctcccgtgttactcaccacggacaactttgtcagtcacaa
      S  L  P  S  K  L  P  P  V  L  L  T  T  D  N  F  V  S  H  K
      #

721  atgagcccgctgccagcccttttgcacagacaagagtttgagggtgaaaaagactagg 781  ggattatagctttgtctctgacgtcattcagtggcagtcctctttgacctcccccgccc
841  tgtccgagctcaccaatccctccccctgaactccactacgtcttgaaccccctggccc
901  ttttctaatgacccnnttaaaccgaacttcttcctgtctgaactcctccaccaccctctgg
961  cacacagacatgccttcacattctttcctgtctgaactcgaacaaaagttaacaatttgcag
1021 tcactgataacaaaggcacaaacacaaacgtcgaacaaaaagagaaggaaaagatgaaag
1081 tgcggttcagtgggatcctttaagcaagtcaagagggacacctagcggaatgttttgtcctgtgga
1141 agatctgtcgtttgcaagtgaagagctgctagttctttagtttgcacctctacctgtaatgggacttcca
1201 agacaactgaaagtgaagagctgctagttctttagtttgcacctctacctgtaatgggacttcca
1261 ggcaaaagaaaatctctgttagttctttagtttgcacctctacctgtaatgggacttcca
1321 cactgtaaggaattatttgtaaaattagattcctgttccagcaccctttgatcacaaac
```

FIG.1B

```
1381  aaaaagcagaaagagtctgcaaattgcacattgccacgattacgtctttgtaagaaa
1441  aaaatgggcactatttttatgaacaatgaacgtgtagcttaaaaaatgtcatggtgc
1501  tagctttgggaatggactcaaagaagagagtggaaaagcacgttttttcttgaatta
1561  ataattaaagctttccgttttaaggaaagtgtgacttttaaaaaaggaaaattttgga
1621  tatggggagctctgcagtggcaatgtcaaggggaaagagtcactgaggaaaatatg
1681  ggctgtgttggcatctaggctcatgtgagtnctagcggctgctattactagtttgcca
1741  gcataagncagcaagggatgacccgagacctagtccctgttcctcctgtcctgaggc
1801  tgctggacacatggagcactatgggacacacatacgggacaccatggacctggattgg
1861  gacagtactatagttcggggacagtacaacctgtttgccatggctttgcggactgttctg
1921  gcaggaagtaacatggcatggactaagaacgagtggggcggccgcgaattc
```

FIG.1C

| | B domain | C domain | A domain | D domain |
|---|---|---|---|---|
| Tilapia | EMAS..AETLCGGELVDALQFVCEDRGFYFSRPT | SRGNNRRPQTR | GIVEECCFRSCDLNLLEQYCA | KPAKSE |
| Sparus aurata | EVAS..AETLCGGELVDALQFVCEDRGFYFSRPT | SRGNNRRPQNR | GIVEECCFRSCDLNLLEQYCA | KPAKSE |
| Rainbow trout | EVAS..AETLCGGELVDALQFVCEDRGFYFSRPT | SRSNSRRSQNR | GIVEECCFRSCDLNLLEQYCA | KPAKSE |
| Chicken | AYGTAETLCGGELVDTLQFVCGDRGFYFSPRV | GRNN.RR.INR | GIVEECCFRSCDLALLETYCA | KSVKSE |
| Human | AYRPSETLCGGELVDTLQFVCGDRGFYFSRPA | SRVS.RR..SR | GIVEECCFRSCDLALLETYCA | TPAKSE |
| Rat | AYRPSETLCGGELVDTLQFVCSDRGFYFSRPS | SRAN.RR..SR | GIVEECCFRSCDLALLETYCA | TPAKSE |
| Mouse | AYGPGETLCGGELVDTLQFVCSDRGFYFSRPS | SRAN.RR..SR | GIVEECCFRSCDLALLETYCA | TPAKSE |
| Sheep | AYRPSETLCGGELVDTLQFVCGDRGFYFSRPS | SRIN.RR..SR | GIVEECCFRSCDLALLETYCA | APAKSE |
| Ancestral vertebrate | ??A?????ETLCGGELVD?LQFVC?DRGFYFSR?? | ?R???RR???R | GIVEECCFRSCDL?LLE?YCA | ???KSE |

| | signal peptide |
|---|---|
| Tilapia | METQQRYGHHSLCHTCRRTQNSRMKVQRMSSTSRALLFALALTLYVV |
| Sparus aurata | METQQRHGRHSLCHTCRRTESSRMKVKKMSSSSRALLFALALTLYVV |
| Rainbow trout | METQKRHEYHSVCHTCRRTENTRMKVKMMSSSNRVLVIALALTLYIV |
| Chicken | MCAARQILLLLLAFLAYALDSAA |
| Human | MGIPMGKSMLVLLTFLAFASCCIA |
| Rat | MGIPVGKSMLVLLISLAFALCCIA |
| Mouse | MGIPVGKSMLVLLISLAFALCCIA |
| Sheep | MGITAGKSMLALLAFLAFASCCYA |

FIG. 2A

E domain

| | |
|---|---|
| Tilapia | RDVSATSLQVIPVMPALKQEVPKKQHVTVKYSKYEVWQRKAAQRLRRGVPAILRARKYKRHAEKIKAKEQA..IFHRPLI |
| Sparus aurata | RDVSATSTQVLPVMPPLKQEVSRKQHVTVKYSKYEVWQRKAAQRLRRGVPAILRAKKYRRQAEKIKAQEQA..IFHRPLI |
| Rainbow trout | RDVSATSLQIIPMVPTIKQDVPRK.HVTVKYSKYEAWQRKAAQRLRRGVPAILRARKFRRQAVKIKAQEQA..MFHRPLI |
| Chicken | RDLSATSLAGLPALN..KESFQKPSH..AKYSKYNVWQKKSSQRLQREVPGILRARYRWQAEGLQAAEEARAMHRPLI |
| Human | RDVS.TPPTVLP......DNFRR..YPVGKFFQYDTW.KQSTQRLRRGLPALLRARRGHVLAKELEAFREAKR.HRPLI |
| Rat | RDVS.TSQAVLP......DDFPR..YPVGKFFKFDTW.RQSAGRLRRGLPALLRARRGWLAKELEAFREAKR.HRPLI |
| Mouse | RDVS.TSQAVLP......DDFPR..YPVGKFFQYDTW.RQSAGRLRRGLPALLRARRGWLAKELKEFREAKR.HRPLI |
| Sheep | RDVS.ASTTVLP......DDFTA..YPVGKFFQSDTW.KQSTQRLRRGLPAFLRARRGRTLAKELEALREAKS.HRPLI |

| | |
|---|---|
| Tilapia | SLPSKLPPVLLTTDNFYSHK*.. |
| Sparus aurata | SLGSKLPPVLLATDNYYNHK*.. |
| Rainbow trout | TLPSKLPPVLPPTDNYVSHN*.. |
| Chicken | SLPSQRPPAPRASPEATGPQE*. |
| Human | ALPTQDPA.HGAPPEMASNRK* |
| Rat | VLPPKDPA.HGASSEMSSNHQ* |
| Mouse | VLPPKDPA.HGASSEMSSNHQ* |
| Sheep | ALPTQDPATHGASSEASSD*.. |

PRODUCTION OF BIOLOGICALLY ACTIVE RECOMBINANT INSULIN-LIKE GROWTH FACTOR II POLYPEPTIDES

RELATED APPLICATION

This application is a continuation-in-part of U.S. patent application Ser. No. 09/003,708 filed on Jan. 7, 1998, which claims the priority of the U.S. Provisional Patent Application No. 60/034,736, filed on Jan. 10, 1997. The contents of said Provisional Patent Application and said U.S. Patent Application are herein incorporated by reference.

FIELD OF THE INVENTION

The present invention (published in *DNA and Cell Biology* (1997), 16:883–892, hereinafter incorporated by reference) relates to a fish insulin-like growth factor II (IGF-II) cDNA and the biologically active IGF-II polypeptide expressed by said cDNA, and more particularly, relates to a recombinant tilapia IGF-II cDNA and the expression of said recombinant IGF-II cDNAs in cells. The IGF-II, signal, and E domain peptides can be produced by gene expression in *E. coli*, yeast, baculovirus, and fish cells or by in vitro synthesis. The E domain peptide has demonstrated mitogenic and anti-tumor effects.

BACKGROUND OF THE INVENTION

Insulin-like growth factors (IGFs) are mitogenic peptide hormones which play important roles in the growth and differentiation of vertebrates. IGFs are translated as a prepropeptide, which can be divided into an N-terminal prepeptide (which is also called a signal or leader peptide), a B to D domain polypeptide (which contains peptides from B, C, A and D domains), and a C-terminal E-domain peptide (which is also called a trailer peptide). The IGF signal and E peptides are proteolytically removed from the B to D polypeptide during protein maturation (Shamblott and Chen (1992), *Proc. Natl. Acad. Sci.* USA, 89:8913–8917). For this reason, the B to D domain polypeptide is also called "the IGF mature peptide".

As of this time, there has been no reports concerning the functions of the IGF signal and E peptides. However, it is well known in the art that a signal peptide may facilitate the transport of protein out of the cell membrane. As for the E peptide, since the E peptide is a part of the IGF preproprotein and may actually be secreted as a part of an intact prohormone, it is possible that the E peptide may affect the processing, transport, or secretion of the mature peptide. It is also possible that the E peptide may indirectly or directly modulate the degradation, receptor interaction, or binding protein interactions of the mature peptide.

There are two kinds of IGFs, namely, IGF-I and IGF-II. IGF-I and IGF-II share high homology of protein folding structure and similar growth promotion effects, even though they are mediated by different IGF receptors (i.e., IGF-I is mediated by a tyrosine kinase receptor, whereas IGF-II is mediated by a mannose-6-phosphate receptor). IGF-I is a 70 amino acid polypeptide which mediates the growth-promoting actions of growth hormone as well as having important local paracrine and autocrine roles in multiple organs (Kavsan et al. (1993), *DNA and Cell Biology*, 12:729–737).

In mammals, the mature form of IGF-II is a neutral protein consisting of 67 amino acid residues with three disulfide bonds. IGF-II is a single-chain polypeptide that contains a $NH_2$—B—C—A—D—COOH domain. The signal peptide and E domain are removed from the mature IGF-II peptide. The cDNA sequences of IGF-II have been reported highly conserved in different mammals, including chickens, sheep, mice, humans, and rats. The mammalian IGF-II is primarily produced in liver during prenatal development under the control of placental lactogen (Gray et al. (1987), *DNA*, 6:283–295). Because of its role as a key component regulating fetal growth, IGF-II is also called a "fetal growth factor".

IGF-II has a complex gene structure. In humans, IGF-II gene consists of 10 exons and spans about 30 kb of DNA. The DNA sequence encoding the mature IGF-II polypeptides in humans is contained within exons 8, 9, and 10. In rat and mouse, IGF-II genes consist of 6 exons and span about 12 kb of DNA and the DNA sequence encoding the prepropeptide of rat or mouse IGF-II is contained within exons 4, 5, and 6.

Up until now, the gene structure and protein function of IGF-II in fish have remained unidentified. IGF-II like peptides have been reported present in the insulin cells of the elasmobranchian endocrine pancreas of fish (Reinneke et al. (1994), *Histochemistry*, 102:365–371). However, whether IGF-II is functioned as autocrine or paracrine is so far unclear. In addition, although so far two IGF-II cDNAs have been discovered in the liver of two fish species: *Sparus aurata* (Duguay et al. (1996), *J. Mol. Endocrinol.*, 16:123–132) and rainbow trout (Shamblott and Chen (1993), supra), there has been no report or study relating to the expression of fish IGF-II in cells as well as the physiological activity of fish IGF-II in vivo.

Furthermore, there has been no report with regard to the findings of IGF-II cDNA in tilapia (*Oreochromis mossambicus*), and the production of a biologically active IGF-II polypeptide from a tilapia cDNA.

The invention to be presented below describes the cloning and sequencing of a fish IGF-II gene and the production of the biologically active fish IGF-II recombinant polypeptides. The establishment of a gene expression system is important because it provides a multifaceted channel for studies of the functional activity of the expressed proteins. In this case, the successful development of a gene expression system for fish IGF-II is especially important because it not only allows for the production of high quality fish IGF-II protein which facilitates the antibody production for immuno-histochemical study (e.g., RIA, ELISA, etc.), but also provides large quantities of fish IGF-II protein for studies of the physiological functions of IGF-II in fish, particularly in determining the stimulatory effects on growth of juvenile fish.

The invention to be present below also discloses the findings concerning the mitogenic and anti-tumor effects of fish IGF-II E domain peptide. The findings are important because they may lead to major breakthrough in human growth and/or cancer prevention.

SUMMARY OF THE INVENTION

The present invention describes (1) the identification of the complete coding region of a fish genomic IGF-II in a cDNA library, (2) the sequence analysis of a fish IGF-II cDNA, (3) the construction of a recombinant fish IGF-II expression vector, (4) the expression of fish recombinant IGF-II peptides in *Escherichia coil* (*E. coli*), yeast, baculovirus, and fish cells, and (5) the biological functions of the fish recombinant IGF-II peptides.

The IGF-II B—D domain peptide, signal peptide, and E domain peptide can be isolated and purified from the host cells (e.g., *Escherichia coli*, yeast, baculovirus, and fish cells) which have the capacity of expressing the vector comprising the IGF-II DNA sequence (SEQ ID NO:1), signal DNA sequence (SEQ ID NO:2), and E domain DNA sequence (SEQ ID NO:3), respectively. These peptides can also be produced by in vitro synthesis.

The functional studies of the E domain peptide (produced either from gene expression or in vitro synthesis) demonstrate that it possesses mitogenic and anti-tumor activities.

DESCRIPTION OF THE PREFERRED EMBODIMENTS

The following embodiments are directed to (1) the findings of fish IGF-II CDNA, (2) the expression of fish recombinant IGF-II polypeptide, (3) the biological activity of fish recombinant IGF-II polypeptides, and (4) the mitogenic and anti-tumor effects of the IGF-II E domain peptide.

Embodiment 1
Findings of Fish IGF-II cDNA

One of the objectives of the present invention is the finding of the coding region of fish IGF-II cDNA. This finding is exemplified by the following procedures, which are directed to, but not limited to, the species of tilapia:

Example 1
Isolation of Fish IGF-II cDNA Clones

Fish IGF-II cDNA clones were selected by a plaque hybridization method using the S domain to E domain of *Acanthopagrus schlegeli* IGF-I cDNA (which was amplified by PCR method) as a probe. A detailed plaque hybridization method using tilapia (hybrid) brain cDNA library as an example is described as follows (Please note that the method described below also applies to the selection of cDNA from the cDNA library of other fish species, e.g., salmon and carp):

First, the S domain to E domain region of *Acanthopagrus schlegeli* IGF-I cDNA was amplified by PCR method. This PCR product, which was approximately 551 bp in length, was further purified by electroelution and used as a hybridization probe.

Second, approximately 1 million recombinant bacteriophages, which were from the tilapia (hybrid) brain cDNA library, were seeded on 12 LB plates. These seeded bacteriophages were then transferred to nylon membranes.

Third, the PCR hybridization probe was then hybridized with said recombinant bacteriophages that sat on the nylon membranes. After a denaturing, renaturing and cross-linking procedure, the hybrids were incubated in a hybridization buffer [containing SDS (7 g/100 ml), 0.5 M EDTA (pH 8.0) (100 µl/100 ml), 50% PEG8000 (20 ml/100 ml), 40% formamide (40 ml/100 ml)] at 37° C. for 16 hrs.

Finally, positive plaques were selected by washing filters in 2XSSC, 0.1% SDS; 0.5XSSC, 0.1% SDS; 0.1XSSC, 0.1% SDS at room temperature, 37° C., and 40° C.

In addition to the above procedures, in vivo excision of the 1S pBluescript phagemid from the Uni-ZAP vector was also used to facilitate recombinant DNA preparation and characterization.

As a result of this plaque hybridization method, a positive tilapia IGF-II cDNA clone was obtained. This positive clone contained pBluescript double-stranded phagemids with the cloned DNA insert, was further used for large-scale plasmid preparation.

Example 2
Isolation of Fish IGF-II Genomic Clones

The fish IGF-II genomic clones were isolated by screening approximately 1 million recombinant bacteriophages from the a fish genomic library with $^{32}$P-labeled fish IGF-II cDNA fragments (the fish genomic DNA library was constructed in phage charon 40 cloning vector) in hybridization buffer (supra) at 42° C. for 16 hrs. The positive plaques were purified and DNA restriction mapping of these positive plaques was further conducted by southern blotting using $^{32}$P-labeled tilapia IGF-II cDNA probes.

Example 3
Nucleotide Sequence Analysis

To analyze the nucleotide sequence of fish IGF-II cDNA, the entire cDNA from a fish species (e.g., tilapia, salmon, and carp) was first digested with PstI restriction enzyme, and then subcloned into pUC18 and transformed into JM109, which was then sequenced by the Sanger dideoxy chain termination method and sequenase kit (USB, version 2.0). To analyze the nucleotide sequence of fish IGF-II genomic DNA, the IGF-II phage DNAs were digested with SacI restriction enzyme, then subcloned into the pBluescript vector and transformed into XL1 Blue *E. coli* host cells.

Finally, a QIAGEN plasmid extraction kit was used to extract DNA and one strand of DNA was sequenced by an ABI autosequencer. The nucleic acid sequences were compared with all published sequences on the Genetics Computer Group computer program.

RESULTS

Figure 1A:
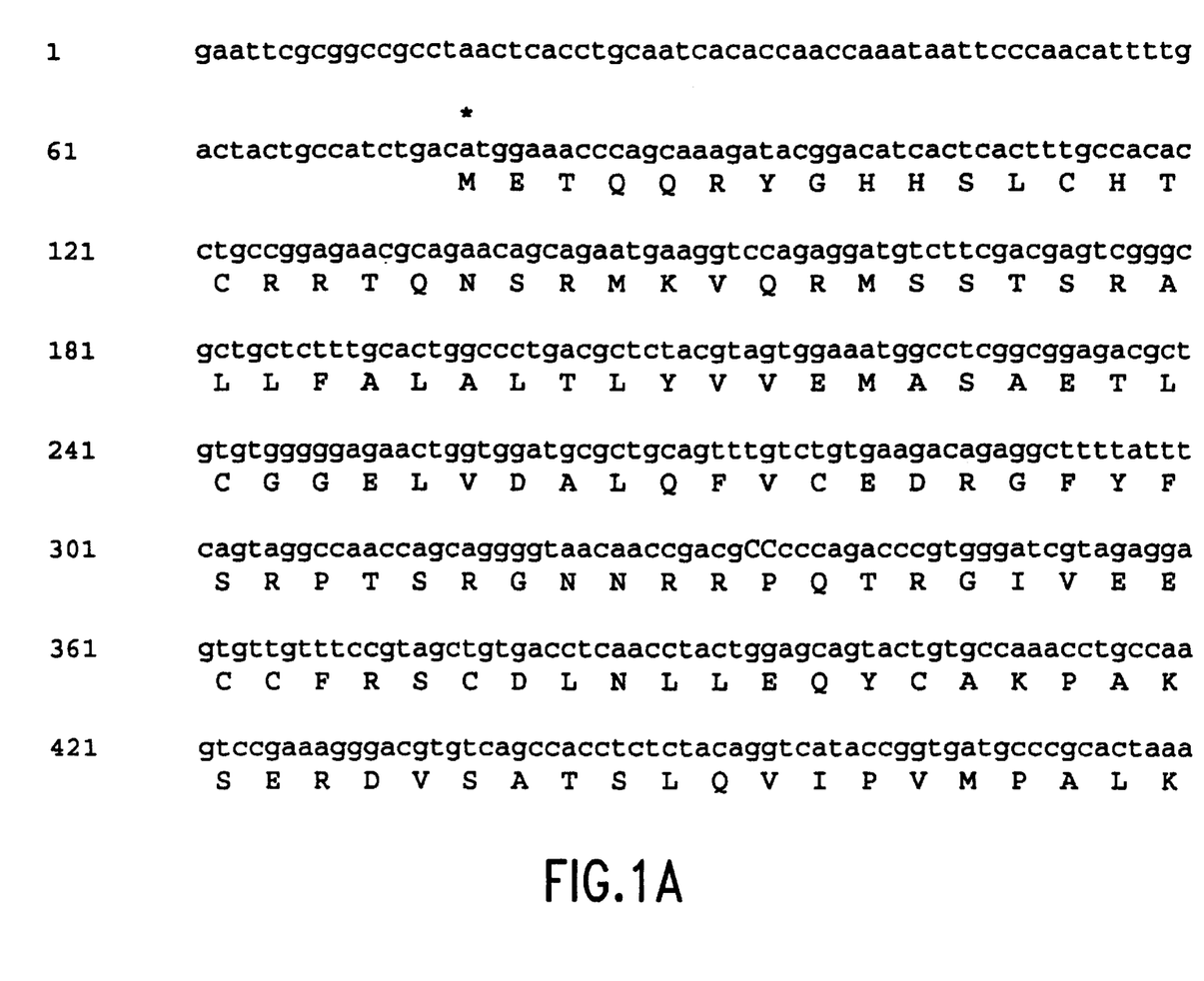
FIG. 1 shows the nucleotide sequence of tilapia (hybrid) IGF-II CDNA and the predicted amino acid sequence of the hormone. The nucleotides are numbered beginning with the first nucleotide at the 5' end. The number on the second line indicates the order of the amino acid position. Asterisk (*), start codon; #, stop codon; n, uncertain cDNA codon.
Figure 1B:
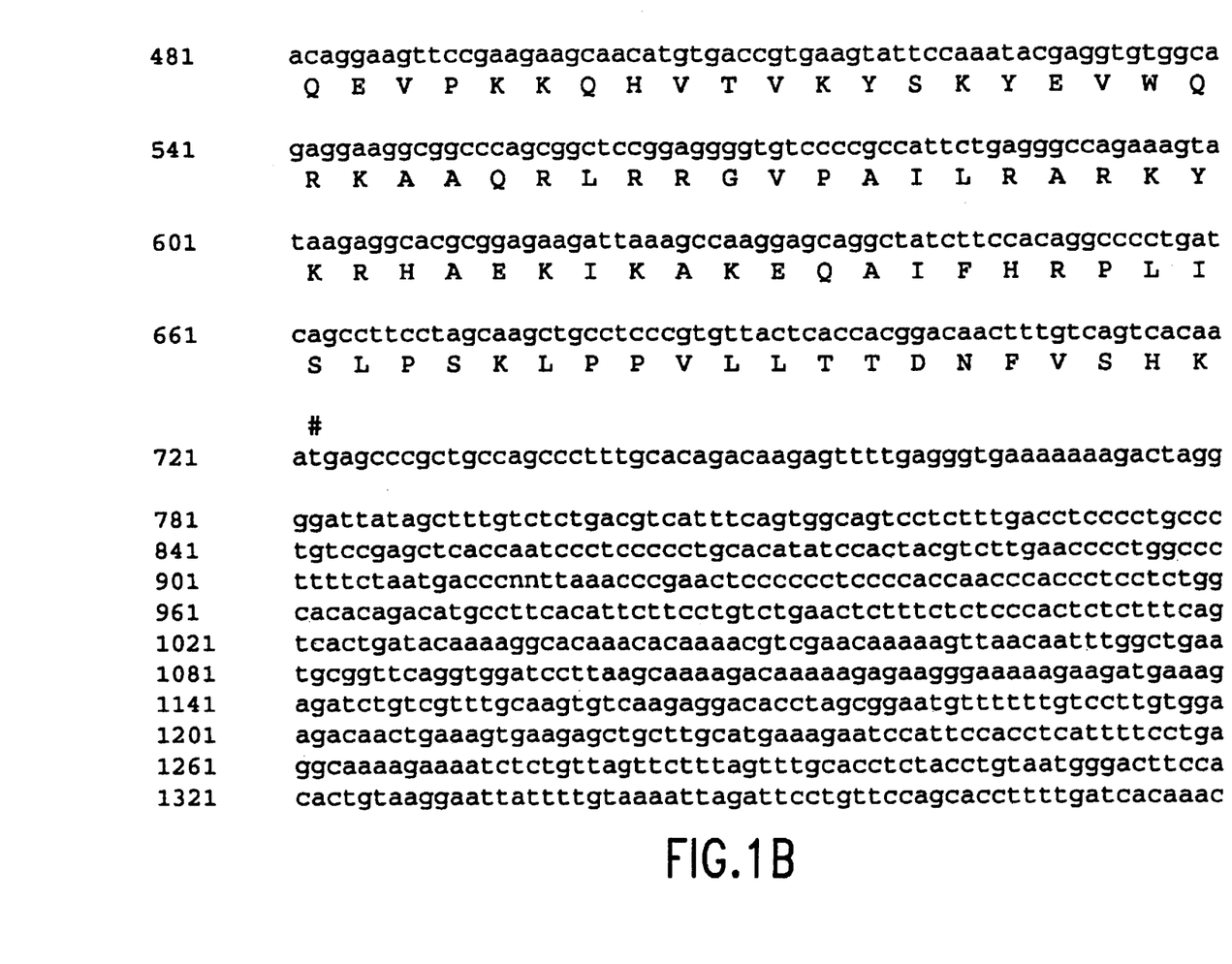
Figure 1C:
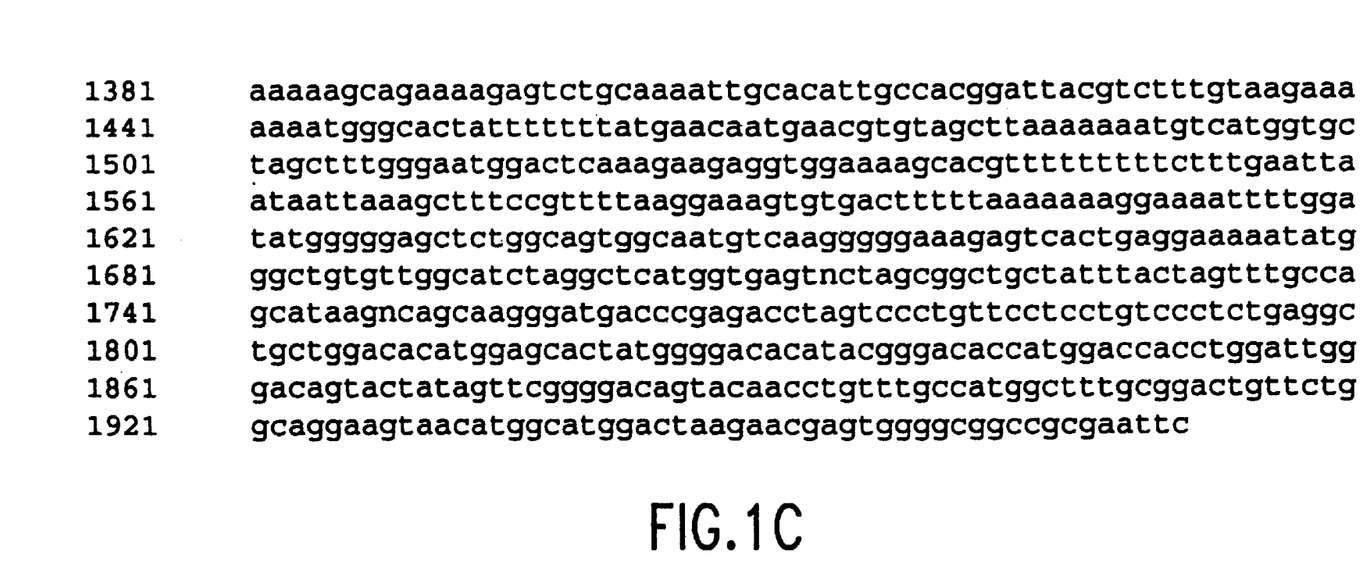

FIG. 1 shows the nucleotide sequence of tilapia (hybrid) IGF-II CDNA and the predicted amino acid sequence of the hormone. The 5' UTR sequence contained a total of 76 nucleotides in length. The 3' UTR sequence contained a total of 1,247 nucleotides in length. The coding region had a total of 645 nucleotides in length.

Tilapia IGF-II polypeptide contained the following peptides:

(1) A signal or leader peptide of 47 amino acid residues (1–47). This signal peptide was encoded by a cDNA having the sequence of SEQ ID NO:2:

5' ATGGAAACCCAGCAAAGATACGGACAT-
CACTCACTTTGCCACCAGTGCCG-
GAGAACGC AGAACAGCAGAATGAAGGTC-
CAGAGGATGTCTTCGACGAGTCGGGCGCTG
CTCTTTGCAC TGGCCCTGACGCTCTACG-
TAGTG.

The signal peptide had the amino acid sequence of SEQ ID NO:5:

Met-Glu-Thr-Gln-Gln-Arg-Tyr-Gly-His-His-Ser-Leu-Cys-His-Thr-Cys-Arg-Arg-Thr-Gln-Asn-Ser-Arg-Met-Lys-Val-Gln-Arg-Met-Ser-Ser-Thr-Ser-Arg-Ala-Leu-Leu-Phe-Ala-Leu-Ala-Leu-Thr-Leu-Tyr-Val-Val.

(2) A B to D domain polypeptide [i.e., the IGF-II mature peptide, in which B domain peptide had 32 amino acid residues (48–79), C domain peptide had 11 amino acid residues (80–90), A domain peptide had 21 amino acid residues (91–111), and D domain peptide had 6 amino acid residues (112–117), respectively]. This IGF-II mature peptide was encoded by a cDNA having the sequence of SEQ ID NO:1:

5' GAAATGGCCTCGGCGGAGACGCTGT-
GTGGGGGAGAACTGGTGGATGCGCTG-
CAGTTTG TCTGTGAAGACAGAGGCTTT-
TATTTCAGTAGGCCAACCAGCAGGGGTAACA
ACCGACGCC CCCAGACCCGTGGGATCGTA-
GAGAGTGTTGTTTCCGTAGCTGTGACCT-
CAACCTACTGGA GCAGTACTGTGCAAACCT-
GCCAAGTCCGAAAG.

The mature peptide (70 amino acids in length) had the amino acid sequence of SEQ ID NO:4:

Glu-Met-Ala-Ser-Ala-Glu-Thr-Leu-Cys-Gly-Gly-Glu-Leu-Val-Asp-Ala-Leu-Gln-Phe-Val-Cys-Glu-Asp-Arg-Gly-Phe-Tyr-Phe-Ser-Arg-Pro-Thr-Ser-Arg-Gly-Asn-Asn-Arg-Arg-Pro-Gln-Thr-Arg-Gly-Ile-Val-Glu-Glu-Cys-Cys-Phe-Arg-Ser-Cys-Asp-Leu-Asn-Leu-Leu-Glu-Gln-Tyr-Cys-Ala-Lys-Pro-Ala-Lys-Ser-Glu.

(3) An E domain peptide of 98 amino acid residues (118–216).

This E peptide was encoded by a cDNA having the sequence of SEQ ID NO:3:

5' AGGGACGTGTCAGCCACCTCTCTACAG-
GTCATACCGGTGATGCCCGCACTAAAACAGG
AAGTTCCGAAGAAGCAACATGTGACCGT-
GAAGTATTCCAAATACGAGGTGTGGCAGAGGA
AGGCGGCCCAGCGGCTCCGGAGGGGT-
GTCCCCGCCATTCTGAGGGCCAGAAAG-
TATAAGA GGCACGCGGAGAAGATTAAAGC-
CAAGGAGCAGGCTATCTTCCACAGGCCCTGATCAGC-
TTCCTAGCAAGCTGCCTCCCGTGTTACT-
CACCACGGACAACTTTGTCAGTCACAAA.

The E peptide had the amino acid sequence of SEQ ID NO:6:

Arg Asp Val Ser Ala Thr Ser Leu Gln Val Ile Pro Val Met Pro Ala Leu Lys Gln Glu Val Pro Lys Lys Gln His Val Thr Val Lys Tyr Ser Lys Tyr Gln Val Trp Gln Arg Lys Ala Ala Gln Arg Leu Arg Arg Gly Val Pro Ala Ile Leu Arg Ala Arg Lys Tyr Lys Arg His Ala Gly Lys Lys Ala Lys Glu Gln Ala Ile Phe His Arg Pro Leu Ile Ser Leu Pro Ser Lys Leu Pro Pro Val Leu Thr Thr Asp Asn Phe Val Ser His Lys

Figure 2A:
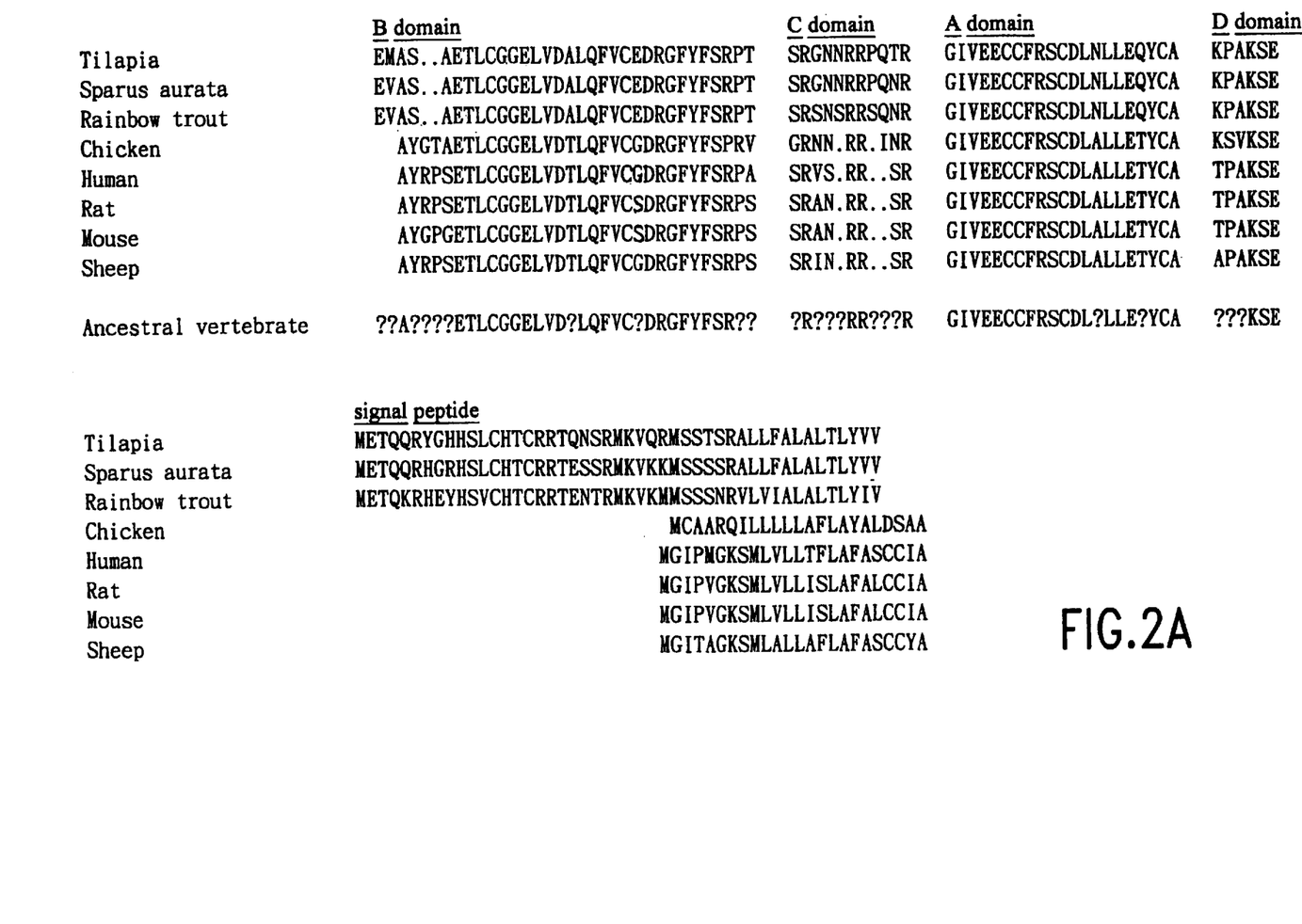
FIG. 2 is a comparison of the amino acid sequences of tilapia IGF-II, Sparus aurata IGF-II, rainbow trout IGF-II, human IGF-II, rat IGF-II, mouse IGF-II, sheep IGF-II, and chicken IGF-II. Sequences start at the first methionine peptide amino acid residue. The IGF-II prepropeptide is divided into the signal peptide, and the B, C, A, D and E domain. A dot (.) represents a gap/deletion.
Figure 2B:
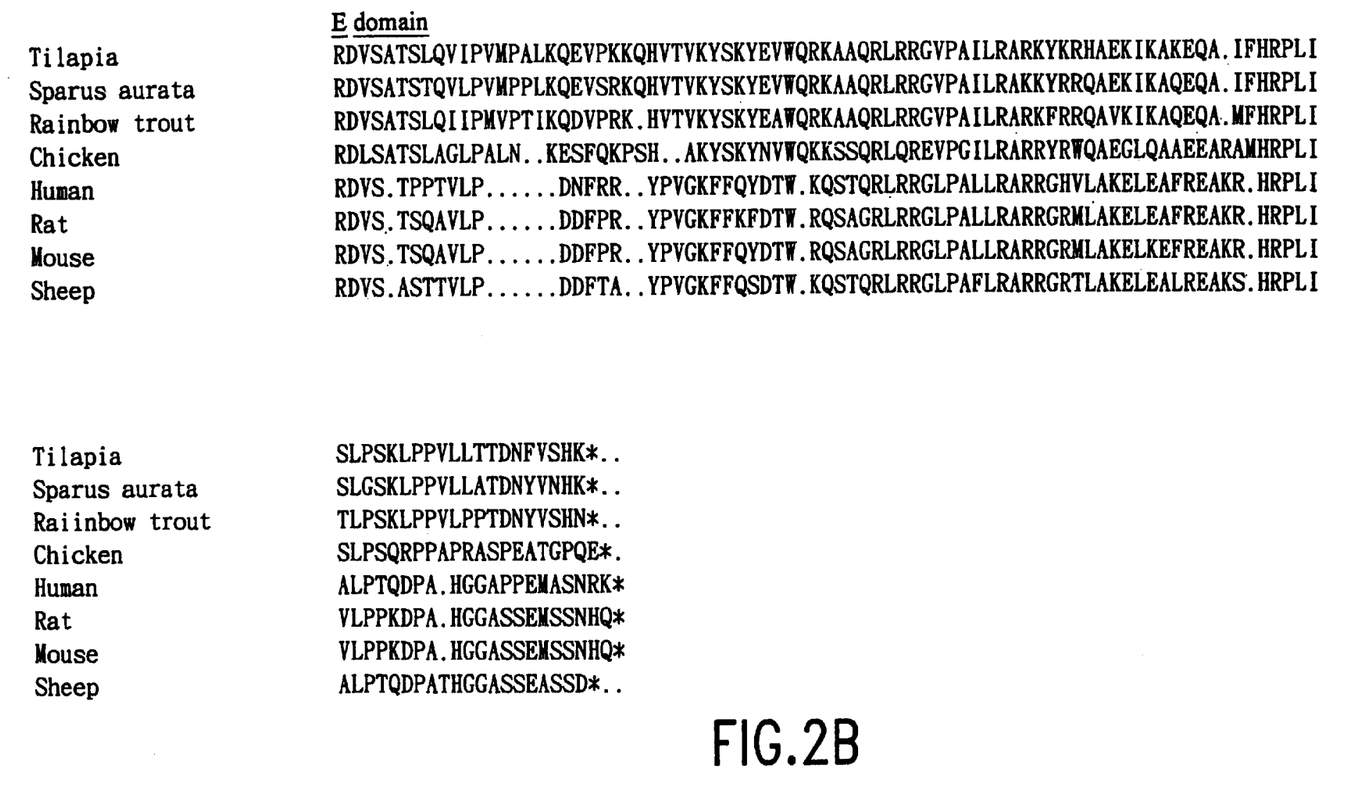

FIG. 2 shows the comparative studies of IGF-II amino acid sequences among different species of animals. Among fish species, the IGF-II mature polypeptide between tilapia and rainbow trout IGF-II (B to D domains) shared a 95.7% similarity and a 92.9% identity. In addition, as comparing the preproproteins (S to E domains) between tilapia and rainbow trout IGF-II, the similarity was 90.7% and the identity was 81.8%.

However, the tilapia IGF-II mature polypeptide, as compared to the mature proteins in chicken, human, rat, mouse, and sheep, only shared 83.1%, 79.1%, 80.6%, 83.6%, and 80.6% in similarities, and 78.5%, 77.6%, 79.1%, 79.1%, and 79.1% in identities, respectively. Also, in comparison with the mammalian IGF-II mature peptides, the tilapia IGF-II mature peptide had a 3-codon insertion at the C domain, and a 2-codon deletion at the B domain. In particular, the tilapia IGF-II at position B22 was a Glu, contrasting to a Ser in rat and mouse and a Gly in humans. The real mechanism with regard to the change of Glu (in fish) to ser (in mouse or rat) to gly (in humans) at B22 is unknown.

FIG. 2 also shows that the tilapia IGF-II mature polypeptide had 5 amino acids differences from those of the other two published fish species (i.e., *Sparus aurata* and rainbow trout): they were: (1) at B2 (in tilapia: Met; in *S. aurata* and rainbow trout: Val); (2) at C3 (in tilapia and *S. aurata*: gly; in rainbow trout: Ser); (3) at C5 (in tilapia and *S. aurata*: Asn; in rainbow trout: Ser); (4) at C8 (in tilapia and *S. aurata*: Pro; in rainbow trout: Ser); and (5) at C10 (in tilapia: Thr; in *S. aurata* and rainbow trout: Asn).

Figure 3:
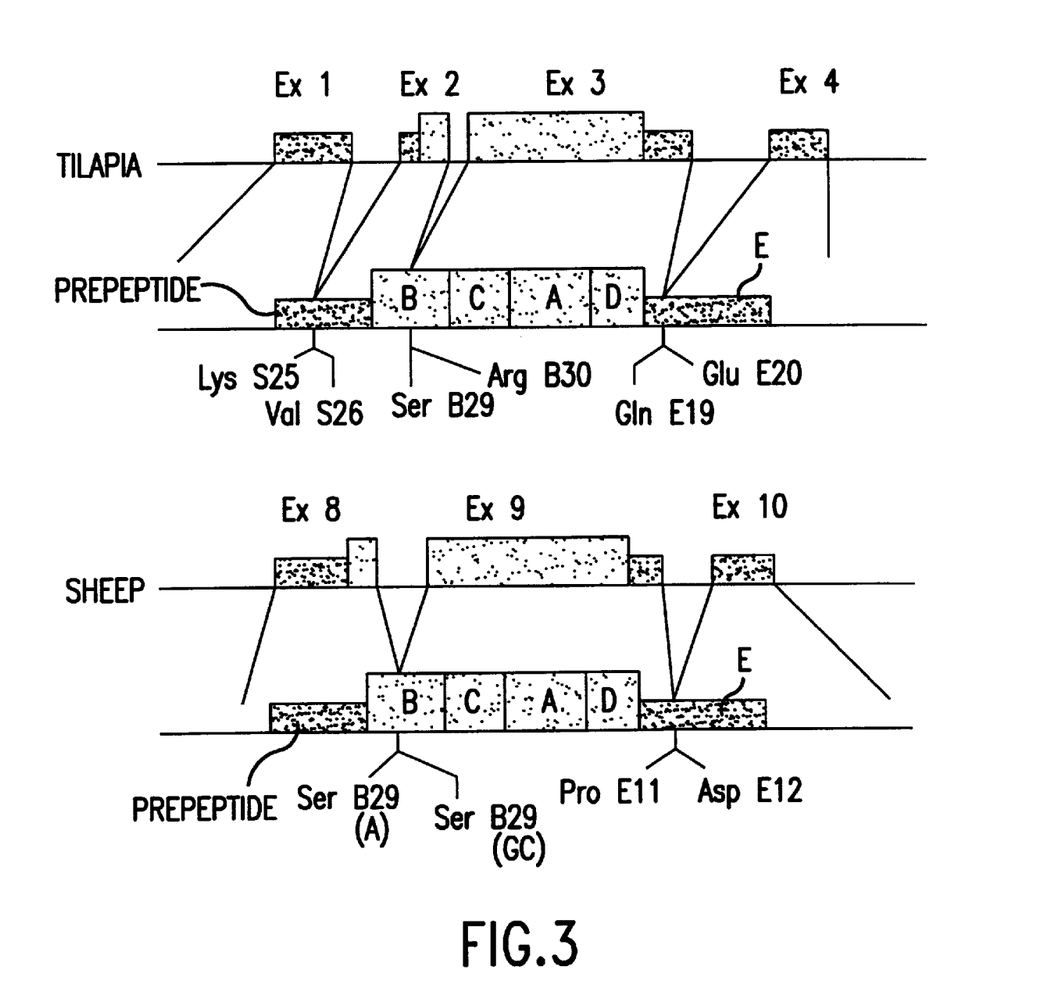
FIG. 3 is a comparison of sheep coding region structure and the organization of the tilapia IGF-II coding region. Exons are shown by boxes, and introns and flanking sequence are shown by thin lines. At the bottom of each structure are the relative locations of the exon and intron boundaries.

FIG. 3 shows the genomic DNA sequences between tilapia and sheep. The genomic DNA sequences of the tilapia coding region were divided into 4 exons (i.e., exons 1–4) and spanned approximately 12.9 kb, contrasting to mammalian IGF-II genes which were comprised of 3 exons. The coding region of tilapia IGF-II gene predicts a prepropeptide of 215 amino acids, including a 47 amino acid signal peptide, a 70 amino acid mature peptide, and a 98 amino acid E peptide. The predicted amino acid sequences of tilapia IGF-II, were consistent to those determined by CDNA sequence data.

Exon 1 of the Tilapia IGF-II gene was from 5' UTR (as compared to the cDNA sequence) to part of the signal peptide (up to S25); exon 2 was from the rest of the signal peptide (S26) to B domain (up to B28); exon 3 was from C domain (C1) to E domain (up to E20); and exon 4 was from E domain to part of the 3' UTR. In other words, exon 1 encoded 25 amino acids, exon 2 encoded 51 amino acids, exon 3 encoded 60 amino acids, and exon 4 encoded 80 amino acids.

Between exons 1 and 2, there was an intron of about 0.8 kb; between exons 2 and 3, there was an intron of about 2.8 kb; and between exons 3 and 4, there was an intron of about 1.3 kb. The sequences of the exon-intron junctions were conformed to the GT-AG rule. The genomic structure of the tilapia IGF-II coding region, which was highly conserved among different fish species, showed great variation as compared with the mammalian IGF-II gene organization, suggesting that a divergence of IGF-II gene structure might have taken place during the evolution of vertebrates.

Embodiment 2

Expression of Fish Recombinant IGF-II Polypeptide

A fish IGF-II CDNA, which has been identified and isolated from the plaque hybridization method as demonstrated in Example 1, is capable of being expressed in various cells to produce a biologically active IGF-II polypeptide. The establishment of a gene expression system for the production of fish recombinant IGF-II polypeptide is exemplified by the following procedures using tilapia as a model (please note that the same procedures can be used to construct a recombinant IGF-II expression vector where the CDNA is derived from other fish species, e.g., salmon and carp):

Example 4
Construction of Recombinant IGF-II Expression vector

A fish IGF-II cDNA containing B to D domains, was amplified by PCR using the following two primers:

Primer 1: 5'-CGGAATTCATATGGAAATGGCCTCGGGCGG AGACGC;

Primer 2: 5'-CGGAATTCCTCATTCGGACTTGGCAGGTTT GGCAC.

These two primers each contained an EcoRI site. The ATG initiation codon was designed in the head of the fish IGF-II B domain, and the stop codon was connected after the final sequence of the fish IGF-II D domain.

There are four kinds of cells that demonstrate expression capability for fish IGF-II cDNA, they are: *E. coli*, yeast, baculovirus, and fish cells. For cloning and expressing fish IGF-II in *E. coli*, the recombinant IGF-II cDNA construct was constructed with a glutathione-s-transferase (GST) gene fusion system (Pharmacia Biotech Co.) of expression vector (pGEX-2T). Both of *E. coli* K12 strains (such as HMS174, HB101, JM109, DH5α and NovaBlue), and B strain (such as BL21, BL21(DE3), B834, B834(DE3)) can be used for the expression and BL21(DE3) is the preferable choice in obtaining the highest quality and quantity of IGF-II polypeptide. For cloning and expressing fish IGF-II in yeast, a *Pichia pastoris* (a methylotrophic yeast) expression kit (Invitrogen Co.) can be used. The Invitrogen *Pichia pastoris* expression systems contain three different kits (namely, the Original Pichia Expression kit, the EasySelect Pichia Expression Kit, and the Multi-Copy Pichia Expression Vectors), each contains a set of vectors, Pichia pastoris strains, and reagents for transformation. In addition, pYES2 vector can be used as an expression vector for *S. cerevisiae* strain INVScl of yeast.

For cloning and expressing fish IGF-II in baculovirus, a MaxBac 2.0 Kit (Invitrogen Co.) can be used. This kit contains baculovirus transfer vectors (pBlueBac4.5, pBlueBacHis2, pBlueBac4.5/CAT [positive control], pVL1392, and pVL1393) and Spodoptera frugiperda (Sf9) insect cells. Additionally, Spodoptera frugiperda ovarian cells (Sf21) cells and High Five cells (BTI-TN-5B1–4) are also recommended for expressing IGF-II. In case that High Five cells are used, pMelBac is the ideal vector for IGF-II gene expression.

For cloning and expressing fish IGF-II in salmon, the IGF-II cDNA construct can be transferred to an expression vector p91023(B) under the control of the adenovirus major late promoter. This expression vector can then be transfected into chinook salmon embryo CHSE-214 cells. The same cloning method also applies to the transfection of IGF-II cDNA construct into tilapia ovary cell line (TO-2 cells).

Example 5
Purification of Fish Recombinant IGF-II Polypeptide in *E. coli*

A fish IGF-II recombinant protein can be purified by the following procedures using an E. coli cell expression system:

(1) inoculating a single colony of BL21(DE3) *E. coli* cells containing a recombinant pGEX-IGF-II plasmid in 100 ml 2X YTA medium (tryptone 16 g/L, yeast extract 10 g/L, NaCl 5 g/L, and ampicillin 100 μg/mL) and incubating said cells at 37° C. for 10 hrs with shaking;

(2) transferring 5 ml of the culture into 500 mL 2X YTA medium and incubated at 37° C. with shaking until the absorbance at 600 nm was 1.1;

(3) adding 0.1M isopropyl-thio-D-galactoside to the culture medium and incubating the culture at 25° C. for 3 hrs with shaking;

(4) centrifuging the culture at 7700 xg for 10 minutes at 4° C. and resuspending the cells by adding 50 μl of ice-cold 1X PBS per milliliter of culture;

(5) disrupting the cells by sonication and adding 1% triton X-100 (final concentration) to the sonicates;

(6) centrifuging the lysed cells at 12,000 xg for 10 minutes at 4° C. and passing the supernatant through a 0.45 μm filter;

(7) aspirating the filtrate into a column (Pharmacia Biotech Co.) and washing the column with 1X PBS, followed by a thrombin solution at 25° C. for 16 hrs;

(8) collecting the reaction mixture which contained the IGF-II protein;

(9) running the reaction mixture on a 15% SDS-PAGE gel to separate the recombinant IGF-II polypeptides from GST protein.

The gel was transferred to a PVDF membrane for further amino acid sequence analysis. Alternatively, the recombinant IGF-II polypeptides on the gel were blotted onto a Hybond™ ECL™ nitrocellulose membrane (Amersham Life Science Co.) and detected by anti-IGF monoclonal antibodies.

RESULTS

To express fish recombinant IGF-II polypeptides in BL21 (DE3) *E. coli* cells containing recombinant IGF-II plasmids, the cells were induced with 0.1 mM IPTG and grown for 3 hrs at 22° C. The total proteins extracted from the above method showed a clear band of 36 kDa (after 30 to 180 minutes of IPTG induction) on the SDS-PAGE gel. This 36 kDa contained the mature IGF-II polypeptide which was bound to a fusion protein GST produced during the IPTG induction. When this 36 kDa protein was further digested with thrombin, a 7 kDa single band protein was produced. ECL western blotting demonstrated that this 7 kDa protein interacted with monoclonal anti-IGF antibody. Amino acid sequence analysis indicated that this 7 kDa protein had additional 7 amino acids before the predicated IGF-II mature polypeptides. Of these 7 additional amino acids, 6 were from the pGEX-2T multiclonal site DNA sequence and the remaining one was an ATG start codon.

Embodiment 3
Biological Activity of Fish Recombinant IGF-II Polypeptides

The biological activity of fish recombinant IGF-II polypeptides were detected both in vitro and in vivo using tilapia ovary cell line TO-2 and juvenile tilapia as examples.

Example 6
Bioactivity of Tilapia Recombinant IGF-II Polypeptides in Tilapia TO-2 Cell Line The bioactivity of tilapia recombinant IGF-II polypeptide was measured in vitro using tilapia ovary cell line (TO-2) by the following procedures [TO-2 cell line was established from ovaries of healthy adult tilapia hybrids (Tilapia mossambica X Tilapia nilotica)]:

(1) seeding TO-2 cells ($3\times10^4$ cells/well) in 24 well-plates containing MEM/F12 medium supplemented with 10% BSA for 24 hrs (serum-free incubation);

(2) further incubating said cells with or without various amounts of IGF-II (0–120 nM) for 18 hrs;

(3) pulse-labelling said cells with [$^3$H] thymidine (2 μCi/mL) for 2 hrs at 25° C.;

(4) adding 0.5 mL of 0.3N NaOH and after standing for 5 minutes, transferring the cell mixture to a scintillation vial to which 5 ml of aquasol was added.

RESULTS

Figure 4:
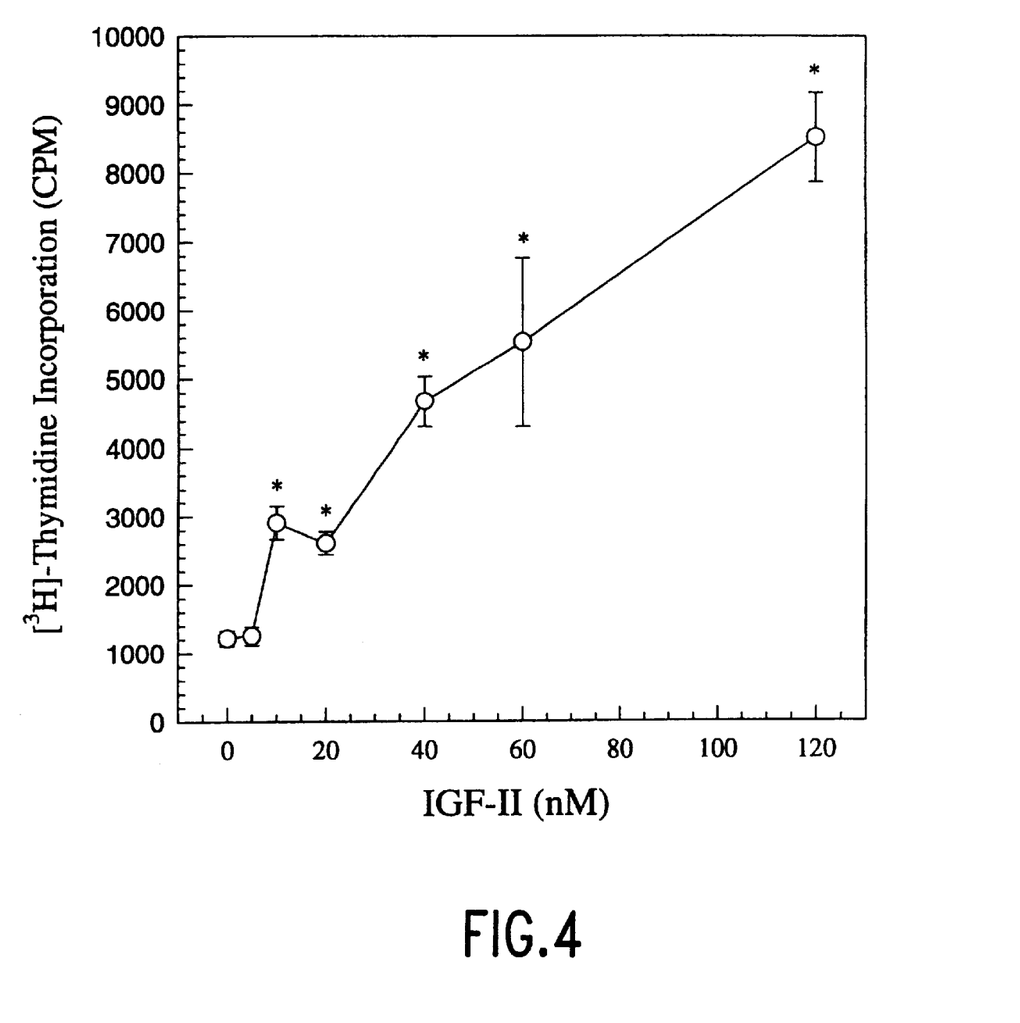
FIG. 4 shows the in vitro stimulatory effects of recombinant tilapia IGF-II polypeptide in tilapia ovary cells (TO-2 cell line).

The result of this experiment is shown in FIG. 4. The test concentrations were between 0 and 120 nM/mL of tilapia recombinant IGF-II proteins. FIG. 4 shows that [$^3$H] incorporation increased proportional to the increase in IGF-II proteins (ANOVA; F=4.46; df.=6.14; P<0.05), suggesting that the stimulatory effect of the tilapia recombinant IGF-II protein is dose-dependent.

Example 7
Effects of Tilapia Recombinant IGFs on Fish Growth

To identify whether tilapia recombinant IGF-II produced by E. coli was biologically active, tilapia with an average of 1.30±0.31 g of body weight and 4.51±0.38 cm of total length were randomly selected. All fish were maintained in freshwater and fed once daily with meal particle (crude protein, 32%; crude lipid, 5%; fiber, 2%; moisture, 9%; Amazon Feed Corp., Taiwan) at a ratio of 5% of total wet weight throughout the experiments. All fish were maintained at room temperature and a 12-hr light, 12-hr dark cycle.

One group of tilapia (20 tilapia per group) was given IGF-II by intraperitoneal injection once a week for a duration of 10 weeks as the experimental group. Another group of tilapia was given no IGF-II injection as control. The amount of IGF-II given was in the concentrations of 0.1, 0.5. 1, and 2 μg per g of body weight per fish. The wet weight and total length of fish were measured once every 2 weeks. Percentages (%) of Body weight gain and body length gain were calculated as (WT-wt) X wt$^{-1}$ X 100; where wt and WT represented initial and final mean wet weight (body length gain was measured as the body length distance from the tip of the lower jaw to the fork (cm)), respectively. All data were analyzed by 1-way analysis of variance.

RESULTS

To determine whether the tilapia recombinant IGF-II expressed in E. coli was biologically active, an experiment which involved the injection of the purified IGF-II polypeptides from E. coli cells into juvenile tilapia was conducted and the growth of the fish, as measured by % weight gain and % length gain, was carefully monitored.

The data show that higher doses of IGF-II polypeptides injection produced greater growth rates in fish, except for 0.1 μg of IGF-II injection which showed insignificant weight gain as compared to the controls. Similarly, the 0.1 μg of IGF-II injection did not produce a conspicuous body length gain.

At the end of the 10 weeks treatment, % of weight gain in each group of tilapia obtaining various amounts of IGF-II injection was as follows:
(1) 2 μg of IGF-II: 259%; (2) 1 μg of IGF-II: 242%;
(3) 0.5 μg of IGF-II: 231%; (4) 0.1 μg of IGF-II: 200%;
(5) Control: 153%.

The results indicated that the highest dose of IGF-II injection (i.e., 2 μg of IGF-II) showed the most % weight gain in tilapia.

The actual wet weight and length (measured as MEAN±SE) in each of the tilapia groups were as follows:
(A) Wet Weight:
(1) 2 μg of IGF-II: 4.67±1.50 g;
(2) 1 μg of IGF-II: 4.45±1.85 g;
(3) 0.5 μg of IGF-II: 4.33±1.30 g;
(4) 0.1 μg of IGF-II: 3.90±0.81 g;
(5) Control: 3.41±0.72 g.
(B) Total Length:
(1) 2 μg of IGF-II: 6.78±0.73 cm;
(2) 1 μg of IGF-II: 6.63±0.76 cm;
(3) 0.5 μg of IGF-II: 6.59±0.66 cm;
(4) 0.1 fig of IGF-II: 5.88±0.47 cm;
(5) Control: 5.81±0.41 cm.

Embodiment 4
Mitogenic and Anti-Tumor Effects of the IGF-II E Domain Peptide A fish IGF-II E domain cDNA, which has been identified and isolated from the plaque hybridization method as demonstrated in Example 1, is capable of being expressed in various cells as described in EMBODIMENT 2 to produce an IGF-II E domain peptide. The IGF-II E domain peptide can be further purified according to the method described in EXAMPLE 5. Furthermore, the IGF-II E domain peptide can be synthesized in vitro. Fish IGF-II E domain peptide (fIGF-II E) has demonstrated both the mitogenic and anti-tumor effects. The mitogenic and anti-tumor effects of the IGF-5 II E domain peptide are determined based upon, but not limited to, the following procedures:

Example 8
Measurement of the Mitogenic Activity of IGF-II E Domain Peptide

The mitogenic activity of IGF-II E domain peptide was measured by adding various concentrations of the purified IGF-II E domain peptide produced from E. coli cells to NIH/3T3 cells and incubating the cells for sufficient amount of time. The NIH/3T3 cells are normal human fibroblasts which are purchased from ATCC.

The proliferation assay was conducted using the proliferation test kit purchased from Boehringer Mannheim Co. Normal proliferation rate is presumed to be 100% of control.

Alternatively, the proliferation assay can be measured by pulse-labeling the NIH/3T3 cells (with or without IGF-II E domain peptide) with 2 μCi/ml [$^3$H]thymidine (Amersham Corp.), followed by treating the cells with cold 10% trichloroacetic acid at 4° C. for 30 minutes to precipitate the DNA material. The proliferation rate can then be determined using a scintillation counter.

Figure 5:
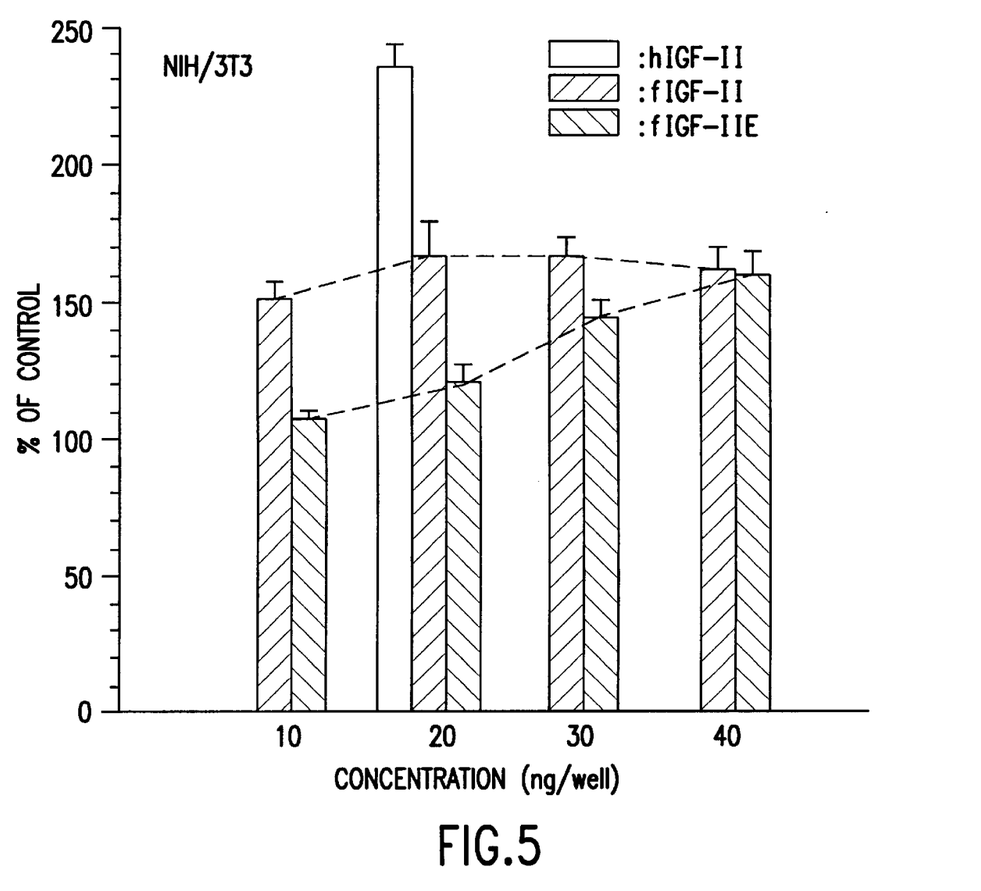
FIG. 5 demonstrates a dose-dependent mitogenic effect of the tilapia IGF-II E domain peptide (fIGF-II E) on NIH/3T3 cells, as compared with human IGF-II peptide (hIGF-II), and tilapia IGF-II peptide (fIGF-II).

As shown in FIG. 5, the proliferation rate (% of control) of 25 NIH/3T3 cells increases proportionally to the amount of the fIGF-II E (ranged from 10 ng to 40 ng per well) added to the cells, suggesting that the mitogenic activity of fIGF-II E is dose-dependent. In contrast, the proliferation rate of NIH/3T3 cells appears to be plateaued at 160% (% of control) when fIGF-II peptide at the concentration of 10 ng–40 ng per well is added. The results of this study confirms that fIGF-II E domain peptide has mitogenic activity.

Example 9
Determination of the Antitumor Activity of IGF-II E Domain Peptide The antitumor activity of IGF-II E domain peptide can be determined in vivo by subcutaneously injecting 5×10$^6$ of human tumor cells into the dorsal flank of female BALC/c nude mice once daily. The tumor cells which can be used in this study include, but not limited to, estrogen dependent breast cancer MCF-7 (ATCC: HTB22), breast carcinoma BT20 (ATCC: HTB19), large cell lung carcinoma NCI-H460 (ATCC: HTB177), lung carcinoma A549 (ATCC: CCL-185), small cell lung carcinoma NCI-H69 (ATCC:

HTB119), prostate carcinomas PC3 (ATCC: CRL1435) and melanoma SK-mel 1 (ATCC: HTB-67).

Before injections, the tumor cells can be trypsinized, followed by twice washed with PBS, and then resuspended in 0.2 ml of PBS. The tumor-injected mice can be monitored twice a week for the appearance of sold tumors.

An effective amount of IGF-II E domain peptide can then be added to the animals when the tumors reach a mean tumor volume of 100–150 mm$^3$. In the control group, saline can be used to replace IGF-II E peptide. After the treatment, tumor growth or regression can be monitored by measuring the perpendicular diameters of the tumors, or alternatively, by observing the cytopathic effects of the tumor cells in the tissue section under the microscope.

It should be understood that the foregoing relates only to preferred specific embodiments of the present invention and that numerous modifications or alterations may be made therein without departing from the spirit and the scope of the invention as set forth in the appended claims.

We claim:

1. An isolated and purified insulin-like growth factor II (IGF-II) peptide comprising the amino acid sequence of SEQ ID NO:4.

2. The isolated and purified IGF-II peptide according to claim 1, wherein said peptide is produced from a host cell containing an expression vector, wherein said expression vector comprises the DNA sequence of SEQ ID NO:1.

3. The isolated and purified IGF-II peptide according to claim 1, wherein said peptide is synthesized in vitro.

* * * * *

SEQUENCE LISTING (1) GENERAL INFORMATION:

(iii) NUMBER OF SEQUENCES:6

(2) INFORMATION FOR SEQ ID NO:1:

(i) SEQUENCE CHARACTERISTICS:
        (A) LENGTH:210 base pairs
        (B) TYPE:nucleic acid
        (C) STRANDEDNESS:BOTH
        (D) TOPOLOGY:BOTH     (ii) MOLECULE TYPE:molecular basis     (iii) HYPOTHETICAL:No     (xi) SEQUENCE DESCRIPTION:  SEQ ID NO:1:

```
GAAATGGCCT CGGCGGAGAC GCTGTGTGGG GGAGAACTGG TGGATGCGCT GCAGTTTGTC      60

TGTGAAGACA GAGGCTTTTA TTTCAGTAGG CCAACCAGCA GGGGTAACAA CCGACGCCCC     120

CAGACCCGTG GGATCGTAGA GAGTGTTGTT TCCGTAGCTG TGACCTCAAC CTACTGGAGC     180

AGTACTGTGC AAACCTGCCA AGTCCGAAAG                                      210
```

(2) INFORMATION FOR SEQ ID NO:2:

(i) SEQUENCE CHARACTERISTICS:
        (A) LENGTH:141 base pairs
        (B) TYPE:nucleic acid
        (C) STRANDEDNESS:BOTH
        (D) TOPOLOGY:BOTH     (ii) MOLECULE TYPE:molecular basis     (iii) HYPOTHETICAL:No     (xi) SEQUENCE DESCRIPTION:  SEQ ID NO:2:

```
ATGGAAACCC AGCAAAGATA CGGACATCAC TCACTTTGCC ACCACTGCCG GAGAACGCAG      60

AACAGCAGAA TGAAGGTCCA GAGGATGTCT TCGACGAGTC GGGCGCTGCT CTTTGCACTG     120

GCCCTGACGC TCTACGTAGT G                                               141
```

(2) INFORMATION FOR SEQ ID NO:3:

(i) SEQUENCE CHARACTERISTICS:
        (A) LENGTH:294 base pairs
        (B) TYPE:nucleic acid
        (C) STRANDEDNESS:BOTH
        (D) TOPOLOGY:BOTH     (ii) MOLECULE TYPE:molecular basis     (iii) HYPOTHETICAL:No     (xi) SEQUENCE DESCRIPTION:  SEQ ID NO:3:

```
AGGGACGTGT CAGCCACCTC TCTACAGGTC ATACCGGTGA TGCCCGCACT AAAACAGGAA        60

GTTCCGAAGA AGCAACATGT GACCGTGAAG TATTCCAAAT ACGAGGTGTG GCAGAGGAAG       120

GCGGCCCAGC GGCTCCGGAG GGGTGTCCCC GCCATTCTGA GGGCCAGAAA GTATAAGAGG       180

CACGCGGAGA AGATTAAAGC CAAGGAGCAG GCTATCTTCC ACAGGCCCCT GATCAGCCTT       240

CCTAGCAAGC TGCCTCCCGT GTTACTCACC ACGGACAACT TTGTCAGTCA CAAA             294
```

(2) INFORMATION FOR SEQ ID NO:4:

(i) SEQUENCE CHARACTERISTICS:
        (A) LENGTH:70 amino acids
        (B) TYPE:amino acid
        (D) TOPOLOGY:Unknown     (ii) MOLECULE TYPE:polypeptide     (iii) HYPOTHETICAL:No     (xi) SEQUENCE DESCRIPTION: SEQ ID NO:4:

```
Glu Met Ala Ser Ala Glu Thr Leu Cys Gly Gly Glu Leu Val Asp Ala
1               5                   10                  15

Leu Gln Phe Val Cys Glu Asp Arg Gly Phe Tyr Phe Ser Arg Pro Thr
            20                  25                  30

Ser Arg Gly Asn Asn Arg Arg Pro Gln Thr Arg Gly Ile Val Glu Glu
        35                  40                  45

Cys Cys Phe Arg Ser Cys Asp Leu Asn Leu Leu Glu Gln Tyr Cys Ala
    50                  55                  60

Lys Pro Ala Lys Ser Glu
65                  70
```

(2) INFORMATION FOR SEQ ID NO:5:

(i) SEQUENCE CHARACTERISTICS:
        (A) LENGTH:47 amino acids
        (B) TYPE:amino acid
        (D) TOPOLOGY:Unknown     (ii) MOLECULE TYPE:polypeptide     (iii) HYPOTHETICAL:No     (xi) SEQUENCE DESCRIPTION: SEQ ID NO:5:

```
Met Glu Thr Gln Gln Arg Tyr Gly His His Ser Leu Cys His Thr Cys
1               5                   10                  15

Arg Arg Thr Gln Asn Ser Arg Met Lys Val Gln Arg Met Ser Ser Thr
            20                  25                  30

Ser Arg Ala Leu Leu Phe Ala Leu Ala Leu Thr Leu Tyr Val Val
        35                  40                  45
```

(2) INFORMATION FOR SEQ ID NO:6:

(i) SEQUENCE CHARACTERISTICS:
        (A) LENGTH:98 amino acids
        (B) TYPE:amino acid
        (D) TOPOLOGY:Unknown     (ii) MOLECULE TYPE:polypeptide     (iii) HYPOTHETICAL:No     (xi) SEQUENCE DESCRIPTION: SEQ ID NO:6:

```
Arg Asp Val Ser Ala Thr Ser Leu Gln Val Ile Pro Val Met Pro Ala
1               5                   10                  15
```

-continued

```
Leu Lys Gln Glu Val Pro Lys Lys Gln His Val Thr Val Lys Tyr Ser
            20              25              30

Lys Tyr Gln Val Trp Gln Arg Lys Ala Ala Gln Arg Leu Arg Arg Gly
            35              40              45

Val Pro Ala Ile Leu Arg Ala Arg Lys Tyr Lys Arg His Ala Glu Lys
        50              55              60

Ile Lys Ala Lys Glu Gln Ala Ile Phe His Arg Pro Leu Ile Ser Leu
65              70              75              80

Pro Ser Lys Leu Pro Pro Val Leu Leu Thr Thr Asp Asn Phe Val Ser
                85              90              95

His Lys
```